United States Patent [19]

Hamilton, Jr.

[11] Patent Number: 4,727,203

[45] Date of Patent: Feb. 23, 1988

[54] TERMINAL TO INTERIOR DOUBLE BOND ISOMERIZATION PROCESS FOR AN OLEFINIC MOLECULE WITH REDUCED DIMERIZATION

[75] Inventor: David M. Hamilton, Jr., Houston, Tex.

[73] Assignee: Shell Oil Company, Houston, Tex.

[21] Appl. No.: 37,375

[22] Filed: Apr. 13, 1987

[51] Int. Cl.⁴ .................................................. C07C 1/00
[52] U.S. Cl. .................................... 585/329; 585/666; 585/670

[58] Field of Search ......................... 585/329, 666, 670

Primary Examiner—Curtis R. Davis
Attorney, Agent, or Firm—Kimbley L. Muller

[57] ABSTRACT

The disclosure of the invention concerns a unique process for the isomerization of a double bond for movement of the same from the alpha position to an internal position of the olefinic molecule. The catalyst utilized for this migration is an 8 and 10 member ring aluminosilicate or tectosilicate having the surface treated with a silane compound.

34 Claims, 1 Drawing Figure

TERMINAL TO INTERIOR DOUBLE BOND ISOMERIZATION PROCESS FOR AN OLEFINIC MOLECULE WITH REDUCED DIMERIZATION

FIELD OF THE INVENTION

Long chained linear alpha olefins are hydrocarbons always in demand in the industrial chemical industry. Such linear alpha olefins can be converted to corresponding alcohols or aldehydes by conventional "OXO" or hydroformylation processes. Resultant $C_{14}$ to $C_{20}$ alcohols can further be ethoxylated with ethylene oxide in the presence of a catalyst to form conventional detergents while lower molecular weight alcohols can be esterified with polyhydric alcohols to form plasticizers of polyvinyl chloride. Also, high chain linear olefins can be converted to alpha olefin sulfonates by treatment with sulfur trioxide and the former then used as biodegradable detergents.

It is most advantageous to formulate higher olefins as a feed material to such processes as hydroformylation from a lower olefin, such as ethylene or butylene. It is also desirable to maximize the specific range of carbon atoms present in the end product. For purposes of utility, it is most desirable to acquire the maximum quantity of $C_{12}$ to $C_{18}$ alpha olefins starting from ethylene. By a preferred modification in known alpha olefin production, in particular in regard to the isomerization catalyst, alpha olefin production can be benefitted. This invention is an improvement upon former processes of high alpha olefin production such as disclosed in U.S. Pat. No. 3,647,906.

BACKGROUND OF THE INVENTION

A basic process to prepare high molecular weight alpha olefins from ethylene is disclosed in aforementioned U.S. Pat. No. 3,647,906, to Farley. This process discloses the combinative treatment of oligomerization of ethylene followed by requisite separation, then isomerization and disproportionation of light olefins and heavy olefins derived from the separation zone. In this manner the specific carbon range of alpha olefins sought is maximized and the refiner's profit margin is greatly increased. All of the specific teachings of this patent are herein incorporated by reference. In the procedure wherein alpha olefins are isomerized to internal olefins, a catalyst is employed which preferably has little or no polymerization or cracking activity. Suitable examples are exemplified as phosphoric acid, bauxite, alumina supported cobalt oxide, or iron oxide or manganese oxide. Other suitable isomerization catalysts are disclosed by the publication "Review of Olefin Isomerization" (H. N. Dunning, Industrial and Engineering Chemicals, 1953). Other isomerization catalysts such as a combination of sodium and potassium on alumina can also be utilized for this type of isomerization process.

In U.S. Pat. No. Re. 28,137 a process is described for preparing an olefin from two dissimilar acyclic olefins in a disproportionation process. It is disclosed that double bond isomerization may occur during this disproportionation. The catalyst for such reactions is a mixture of molybdenum oxide and alumina containing cobalt oxide and optionally containing minor amounts of alkali metal or alkaline earth metal ions. Also, suitable rhenium heptoxide is utilized in these type of disproportionation reactions. Such molybdenum or rhenium catalyst prepared on a support comprising various forms of alumina are exemplified in U.S. Pat. No. 3,471,586, Lester.

Types of aluminosilicates have previously been used for skeletonal isomerization of hydrocarbon molecules including olefins. U.S. Pat. Nos. 4,217,240; 4,257,804; and 4,272,409 are exemplary of certain isomerization catalysts. An article in the *Journal of Catalysis*, Volume 92 (1985), describes the use of a ZSM-5 zeolite for the isomerization of 1-hexene. The double bond shift discovered therein formed both the cis- and trans-2-hexene. The skeletal rearrangements which give cis-3-methyl-2-pentene and trans-3-methyl-2-pentene are the result of the skeletal rearrangements of the hexene-1. The performance of the ZSM-5 zeolite was found to be comparable to the catalytic isomerization of 1-hexene in the presence of an HY zeolite while the rate of conversion was substantially less. See also Wojciechowski et al, *International Journal of Chemical Kinetics* Vol. 15 (1983) and Abbot, *Canadian Journal of Chemical Engineering* Vol. 63 (1985), Catalytic Cracking and Skeletal Isomerization of N-hexene on ZSM-5 Zeolite. In October 1985, Abbot and Wojciechowski discussed the summary of the catalytic reactions of normal hexenes in the presence of amorphous silica-alumina. See the *Canadian Journal of Chemical Engineering*, Vol. 63 (1985). The predominant isomerization is skeletal with very low initial selectivity to cracking. The slowness of reaction to paraffins and dehydrogenated species is attributed to a small number of strongly acidic sites on the amorphous material. The skeletal isomerization is specifically discussed at page 819 of that article.

A ferrierite aluminosilicate is exemplified by U.S. Pat. Nos. 4,016,245 and 4,343,692 although the catalyst of the latter patent is taught as piperidine-derived and is useful in a catalytic dewaxing process. Incorporated by reference herein is the disclosure of Nanne et al, U.S. Pat. No. 4,251,499, which describes the preparation of a piperidine derived ferrierite. Also, an ethylenediamine and pyrollidine derived ferrierite is exemplified in aforementioned U.S. Pat. No. 4,016,245.

A method for the production of surface modified zeolites was disclosed in U.S. Pat. No. 4,451,572, issued to Cody, all of the teachings of which are herein incorporated by reference. Specific references can be made to Col. 8 and 9 for the technique of how to perform the silylation. The organosilanes of the general formula:

$$SiR_yX_{4-y}$$

and $$(RwX_{3-w}Si)_2\text{-}Z$$

are useful as feasible silylation agents wherein:
 y=1 to 4
 w=1 to 3
 R=alkyl, aryl, alkoxy, arylalkyl, and where R has from 1 to 10 carbon atoms
 x=halide and
 Z=oxygen, NH- or substituted amines or amides.

The zeolites treated by this silylation technique to modify their surface are typical large pore zeolites as exemplified by X, Y, and ZSM-5 aluminosilicates. There is not present the disclosure of treating an aluminosilicate having a ring structure commensurate with an 8 and 10 member ring channel. There is also no recognition that the treatment of the aluminosilicates will diminish dimerization reactions in an olefin isomerization reaction.

OBJECTS AND EMBODIMENTS

It is an object of this invention to provide a new combinative catalytic isomerization process in order to maximize the quantity of particular carbon range alpha olefins from an ethylene feed material.

Another object of this invention is to provide a double bond isomerization process for the movement of alpha position olefin bonds to an interior position in the presence of a specific and select type of aluminosilicate having a channel size restrictive so as to prevent aromatization or alkylation of the olefin molecule.

Another object of this invention is to provide a sequential process for the maximal preparation of $C_{12}$ to $C_{18}$ alpha olefins from a feed material comprising ethylene by the oligomerization of ethylene and subsequent isomerization and disproportionation of select lighter and heavier fractions of the oligomerization zone effluent stream.

Another object of this invention is to isomerize a combined feedstream of $C_4$ to $C_{10}$ olefinic hydrocarbons and $C_{20}$ to $C_{100}$ olefinic hydrocarbons, with said feedstream being balanced to approximately $C_{12}$ by the addition of $C_4$ olefins, in the presence of select aluminosilicate zeolites having a channel size sufficient to permit double bond isomerization from the alpha position to an internal position and selective to prohibit aromatization and alkylation in the channel.

One embodiment of this invention resides in a double bond isomerization process for movement of a double bond possessed by an olefinic molecule from an alpha position to an interior position in the molecule, which process comprises contacting at least one olefin having an alpha double bond therein with a select aluminosilicate having a channel size sufficient to permit said double bond isomerization and a channel size restrictive to prevent aromatization or alkylation of said olefin molecule within said channels of said aluminosilicate, at isomerization conditions, and to thereby move said double bond from said alpha position to an interior position.

Another embodiment of this invention resides in a process for the increased production of higher olefins having alpha double bonds from ethylene which comprises: oligomerization of a feed material predominately comprising ethylene in an ethylene oligomerization zone, at oligomerization conditions, in the presence of an oligomerization catalyst, to form higher olefinic molecules having even carbon numbers of from $C_4$ to $C_{100}$; separating said produced even numbered olefins in a first separation zone to form a first olefin product stream having alpha double bonds and having from $C_{12}$ to $C_{18}$ and first separation zone effluent stream having alpha olefins of from $C_4$ to $C_{10}$ and heavy alpha olefins having from $C_{20}$ to $C_{100}$; combining said light and said heavy alpha olefins and passing said combined stream to purification-isomerization-disproportionation steps and balancing therewith by the addition of a quantity of $C_4$ olefins to average the carbon number in said combined stream to approximately $C_{12}$; purifying said combined alpha olefin stream in the presence of a purification absorbent bed, at purification conditions, to remove from said combined stream impurities comprising oxygenates, metals, water and inorganics; double bond isomerizing, in an isomerization step, said purified alpha olefins, at isomerization conditions, in the presence of a select aluminosilicate catalyst having a channel size sufficient to permit said isomerization and a channel size restrictive to prohibit aromatization and/or alkylation of said olefin molecule within said channels of said aluminosilicate to produce an isomerization effluent stream having internal double bonds and being substantially free of alpha-situated double bonds; disproportionating said isomerization olefin stream in a disproportionation step in the presence of a disproportionation catalyst maintained under disproportionation conditions to form an effluent stream containing $C_{11}$-$C_{14}$ olefins; and separating said disproportionation effluent stream in a second separation zone to form a second olefin product stream having some alpha double bonds and having from $C_{11}$-$C_{14}$ and a light and heavy olefin fraction.

BRIEF DESCRIPTION OF INVENTION

This invention is a novel catalytic process to force movement of an alpha position double bond of an olefinic molecule to an interior position within said molecule by contacting the olefinic molecule, at isomerization conditions, in the presence of a select aluminosilicate having a channel size sufficient to permit double bond isomerization and a channel size sufficient to prohibit aromatization or alkylation of the olefinic molecule within the channels of the select aluminosilicate. This double bond isomerization process is a modification to an overall three-step oligomerization, isomerization and disproportionation process used to produce a maximum quantity of $C_{12}$ to $C_{18}$ alpha olefins from an ethylene feed material. The surface of the aluminosilicate is silylated to reduce dimerization during isomerization.

DETAILED DESCRIPTION OF THE INVENTION

Select linear alpha olefins, particularly in the carbon range of $C_{12}$ to $C_{18}$, can be produced from ethylene in an improved catalytic process having three essential integrated process steps of (1) oligomerization, (2) isomerization, and (3) disproportionation. Additional internal olefins can also be arrived at by recycle to particular segments of an overall closed loop process flow scheme. The crux of this overall process is a novel catalytic isomerization step, wherein a select aluminosilicate catalyst is provided comprising an aluminosilicate having specific select channel size to thereby restrict aromatization and alkylation of the olefinic molecule while providing encouragement for the isomerization for the alpha olefin double bond to an internal position.

In the isomerization zone, high alpha olefins and lower alpha olefins are blended and balanced to a $C_{12}$ carbon atom range by the addition of butene whereafter the alpha olefins are converted to internal olefins by double bond isomerization. The isomerization double bond migration procedure is carried out at isomerization conditions, including a gas or liquid phase and at a temperature of from about 0° C. to about 500° C., a pressure of from about 1.0 psia to about 2000 psia and a weight hourly space velocity of from 0.1 to about 20. The preferred isomerization conditions include a temperature of from about 100° C. to about 150° C., a pressure of from about 14 psia to about 2000 psia and a weight hourly space velocity of 0.1 to about 20. The alpha olefins are isomerized in the presence of a select aluminosilicate catalyst having specific channel size for penetration of specific molecules while prohibiting others to enter and undergo such reactions as aromatization or alkylation. The preferred aluminosilicate catalyst is a ferrierite aluminosilicate catalyst defined as a ferrierite having 8 and 10 member ring channels. These ferrierite catalysts may be exemplified by the ZSM-35 aluminosilicate of U.S. Pat. No. 4,016,245 or most preferably by a piperidine derived ferrierite as discussed in U.S. Pat. No. 4,251,499, Nanne et al. Other zeolites of sufficient channel size such as Theta-1 are also viable for this type of conversion. Other aluminosilicates maybe exemplified by ZSM-12, ZSM-22, ZSM-23 and ZSM-48. These aluminosilicates may be associated with a catalytic metal, preferably selected from Group VIII or Group VIB of the Periodic Table. These metals may be exemplified by palladium, platinum, ruthenium, nickel, cobalt, molybdenum, osmium and may be present in combination with one another. These catalytic metals will be present in a quantity of from 0 wt% or 0.1 wt% to about 25 wt% with particular emphasis placed on the type and quantity of catalyst to maximize isomerization and mitigate dimerization.

It has been determined that the olefin isomerization reaction in the presence of the 8 and 10 member ring channel aluminosilicates can be accompanied by undesirable dimerization reactions. It has now been discovered that these undesirable dimerization reactions can be controlled by treatment of the surface of the aluminosilicate. The compound that is used to reduce the dimerization reaction can be selected from any compound which will mask the dimerizing agents found on the surface of the aluminosilicates. These agents may be selected from silane compounds or pyridine although the former are most preferred to avoid other problems of isomerization interference.

Either methylsilylating agents or organofunctional silylating or silane agents may be used to treat the aluminosilicates of this invention. These silane agents are believed responsible to modify the catalytic sites on the aluminosilicate surface and thereby to reduce access to dimerization sites for the alpha olefin feed material. A potential list of possible silane agents is set forth in Kirk-Othmer Vol. 18 at pages 260–268, all of the teachings of which are hereby incorporated by reference. These compounds include the following:

of an 8 and 10 member ring aluminosilicate with HMDS produced a surprising and unexpected reduction in the dimerization of the olefinic molecule.

The instant isomerization of the alpha olefin double bond is a non-skeletal isomerization, which may be exemplified by the isomerization of 1-decene. During this isomerization, the double bond at the 1 position is moved to the 8-2 position, 7-3 position, 6-4 position and the 5 position. Where the isomer distribution is attained at 80 to 100% of the calculated isomer distribution, this equilibrium will comprise from about 20% to about 30% at the 8 and 2 position, about 20% to about 25% at the 7 and 3 position, about 25% to about 35% at the 6 and 4 position and about 10% to about 15% at the 5 position. A small residual amount (less than 1%) of the alpha olefin may also be present. These particular internal olefins are disproportionated to form the select $C_{11}$ to $C_{14}$ olefins, which can undergo hydroformylation to alcohols and aldehydes.

The oligomerization zone has ethylene or another even number lower olefin fed thereto to prepare long chain linear alpha olefins. This zone is conducted and maintained at oligomerization conditions comprising a temperature of from about 65° C. to about 120° C. and a pressure of from about 1000 psig to about 2000 psig. It is standard practice to employ an oligomerization catalyst to maximize the amount of linear alpha olefins produced. It is conceivable that the alpha olefins have a carbon range of from about 4 to as high as 100. Suitable oligomerization catalyst include Ziegler-type catalysts such as lithium, sodium, potassium, beryllium and magnesium metal catalysts. Suitable Ziegler-type catalysts employed in ethylene oligomerization are described in U.S. Pat. Nos. 2,699,457; 3,310,600; 3,478,124 and 3,482,000, all of the teachings of which are incorporated herein.

Another suitable class of ethylene oligomerization catalysts are nickel chelates of phosphorus containing bidentate ligands. A specific example of these catalysts are nickel chelates of bidentate ligands having a tertiary organophosphorus moiety and a carboxymethyl or carboxyethyl group attached directly to the phosphorus

| Chemical Name | Formula |
|---|---|
| Silane Coupling Agents | |
| vinyltriethoxysilane | $CH_2=CHSi(OC_2H_5)_3$ |
| vinyltris($\beta$-methoxyethoxy)silane | $CH_2=CHSi(OCH_2CH_2CH_2OCH_3)_3$ |
| vinyltriacetoxysilane | $CH_2=CHSi(OOCCH_3)_3$ |
| $\gamma$-methacryloxypropyltrimethoxysilane | $CH_2=C(CH_3)COO(CH_2)_3Si(OCH_3)_3$ |
| $\gamma$-aminopropyltriethoxysilane | $H_2NCH_2CH_2CH_2Si(OC_2H_5)_3$ |
| Silylating Agents | |
| trimethylchlorosilane | $(CH_2)H_3SiCl$ |
| n-trimethylsilydimethylamine | $(CH_3)_3SiN(CH_3)_2$ |
| hexamethyldisilazane | $(CH_3)_3SiNHSi(CH_3)_3$ |
| n-trimethylsilylacetamide | $CH_3CONHSi(CH_3)_3$ |
| bis(trimethylsilyl)acetamide | $CH_3C$ $OSi(CH_3)_3$ $NSi(CH_3)_3$ |
| bis(trimethylsilyl)trifluoroacetamide | $CF_3C$ $OSi(CH_3)_3$ $NSi(CH_3)_3$ |
| dimethylchlorosilane | $(CH_3)_2HSiCl$ |
| tetramethyldisilazane | $(CH_3)_2HSiNHSiH(CH_3)_2$ |
| bromomethyldimethylchlorosilane | $BrCH_2(CH_3)_2SiCl$ |
| chloromethyldimethylchlorosilane | $ClCH_2(CH_3)_2SiCl$ |
| di(chloromethyl)tetramethyldisilazane | $ClCH_2(CH_2)SiNHSi(CH_3)_2CH_2Cl$ |

1,1,1,3,3,3,-hexamethyldisilazane, commonly nomenclated as HMDS, is preferred and is exemplified in the illustrative embodiment which follows. The treatment atom of the organophosphorus moiety.

The effluent from the oligomerization zone contains olefins having from $C_4$ to $C_{100}$. The exact distribution is dependent upon the conditions in the oligomerization zone and the catalyst selected to give initiative to the formation of the long chain olefins. It is desirable to maintain the oligomerization zone under conditions sufficient to maximize the quantity of $C_{12}$ to $C_{18}$ alpha olefins. This effluent is passed to a first separation zone which is maintained under conditions of $-10°$ C. to about 300° C. and a pressure of from about 0.4 psia to about 650 psig. The separation of the olefins is made in a separation zone to acquire a first alpha olefin product having from 12 to 18 carbon atoms. Two other streams are formed in the first separation zone, one being a light olefin stream having from $C_4$ to $C_{10}$ and the second being a heavy olefin stream having $C_{20}$ to $C_{100}$. This process seeks to recapture these lighter and heavier olefins from the separation zone and reprocess them to a desired carbon range of 11 to 14. These two streams are blended and will be converted in a purification-isomerization-disproportionation zone to modify the same to the desired $C_{11}$ to $C_{14}$. For this reason, this combined effluent stream of light and heavy olefins is blended with a $C_4$ olefin in an amount calculated to average $C_{12}$.

This combined stream is passed to a purification zone wherein the stream is purged of isomerization and disproportionation catalyst poisons comprising oxygenates, metallic ions, water and inorganics via this purification. It is preferred that the nefarious unwanted compounds are absorbed on an absorbent comprising a refractory inorganic oxide. This inorganic oxide may be alumina, silica, zirconia, magnesia, silica-alumina, silica-alumina-chromium, etc. The only requirement of this absorbent bed is that it be selective for the absorption of these problem compounds while permitting elution of the olefins to the isomerization zone. It is contemplated that these impurities may be drained from the purification zone and the absorbent may be regenerated in any convenient manner in order to renew or replace the refractory inorganic oxide absorbent.

The effluent derived from the purification zone, i.e. purified olefins having carbon ranges from $C_4$ to $C_{10}$ and $C_{20}$ to $C_{100}$ and balanced to $C_{12}$ are added to the isomerization zone above discussed wherein the preferred aluminosilicate isomerization catalyst of this invention will modify the alpha olefins to interior olefins. An isomerization equilibrium is eventually arrived at with the double bond migrating between different positions in the olefin molecule. The isomerization, which is undertaken in the isomerization step, is one that is not considered skeletal. This type of movement of the double bond has heretofore not been recognized in the presence of a select ferrierite type catalyst, which has been silylated with a silylation or silane agent.

The effluent passing from the isomerization step is a compilation of different internal olefins with a near absence of alpha olefins. These olefins molecules are rearranged in a disproportionation zone such that the higher molecular weight olefins are reacted with lower molecular weight olefins to yield olefins of intermediate molecular weight but with the preferred length of the molecule being $C_{11}$ to $C_{14}$. By way of illustration, a higher olefin such as a 15-triacontene reacted with 2-butene is disproportionated into two molecules of 2-heptadecene. Similary, 4-tetracosene is disproportionated in the presence of 2-butene into 2-hexene and 1-heneicosene.

The disproportionation step is performed under disproportionation conditions which include a reaction temperature of from about 100° C. to about 150° C. and a pressure of from about 150 psig to about 250 psig. The disproportionation is performed in the presence of a disproportionation catalyst which may be exemplified by cobalt and molybdenum metals deposited on an inorganic oxide support. These metals may be present in a weight percent of from about 1 wt% to about 15 wt% of molybdenum and from about 0 wt% or 0.1 wt% to about 5 wt% of cobalt. It is also possible that this catalyst be admixed with an alkali or alkaline earth metal to further the disproportionation. Other disproportionation catalysts will include Group VIIB oxides such as rhenium supported on a refractory inorganic oxide such as alumina or silica. The diproportionation reaction is usually effected in a liquid phase in the presence of ethylene and if desired, liquid reaction diluents are utilized. Illustrative of suitable diluents are hydrocarbons free from aliphatic unsaturation, such as acyclic or alicyclic alkenes of from 6 to 12 carbon atoms, i.e., hexane, isooctane and cyclohexane. Also exemplary would be monoaromatic compounds such as benzene and toluene. If the diluent is added, it is present in amounts up to 20 moles of diluent per mole of olefinic reactants.

It should also be appreciated that the olefin products from the disproportionation zone will contain even and odd number carbon atoms whereas only even numbered olefins are produced in the ethylene oligomerization zone. It is also feasible to combine the isomerization and disproportionation step into one unitary reaction containing the select aluminosilicate catalyst of the isomerization zone and the preferred disproportionation catalyst of the disproportionation zone. In the event of simultaneous isomerization and disproportionation, the reaction conditions will depend in part upon the particular catalyst employed but generally will include a temperature of 25° C. to 300° C. and a pressure which may vary from about 1 atmosphere to about 80 atmospheres. The olefins are contacted for a period of time of from about 30 minutes to 1000 hours. The catalyst may be present in a pellet form with the isomerization and disproportionation catalyst being impregnated on a single pellet. The catalysts may be physically admixed and added to a unitary isomerization-disproportionation zone.

The reactor effluent from the disproportionation zone is passed to a second separation zone maintained at separation conditions of from about 30° C. to about 350° C. and a pressure of from about 1 psia to about 200 psia. A second higher olefin product stream is withdrawn from the second separation zone similar to the high olefin product stream derived from the first separation zone. These olefins may be mixed in tandem or sold individually as high olefin product streams. The second separation zone will function in a similar manner to the first separation zone in that a light olefin having from $C_4$ to $C_{10}$ and a heavy olefin fraction having from $C_{15}$ to $C_{100}$ will be produced. It is possible that these streams can be further combined and processed in the same manner as the two non-product streams acquired from the first separation zone. In order to maximize the productivity of $C_{11}$ to $C_{14}$ olefins, the latter recombination step will be undertaken or these olefins may be recycled to the process. In the event the heavy olefins having from $C_{15}$ to $C_{100}$ are recycled, it is preferred that they be combined with the heavy and light olefin derived from the first separation zone before admixture with the $C_4$ olefin to acquire the average carbon number of 12. If the recycle of the second separation stage light olefins is desired, this may be charged to the isomerization zone for further processing.

DETAILED DESCRIPTION OF THE DRAWING

Figure 1:
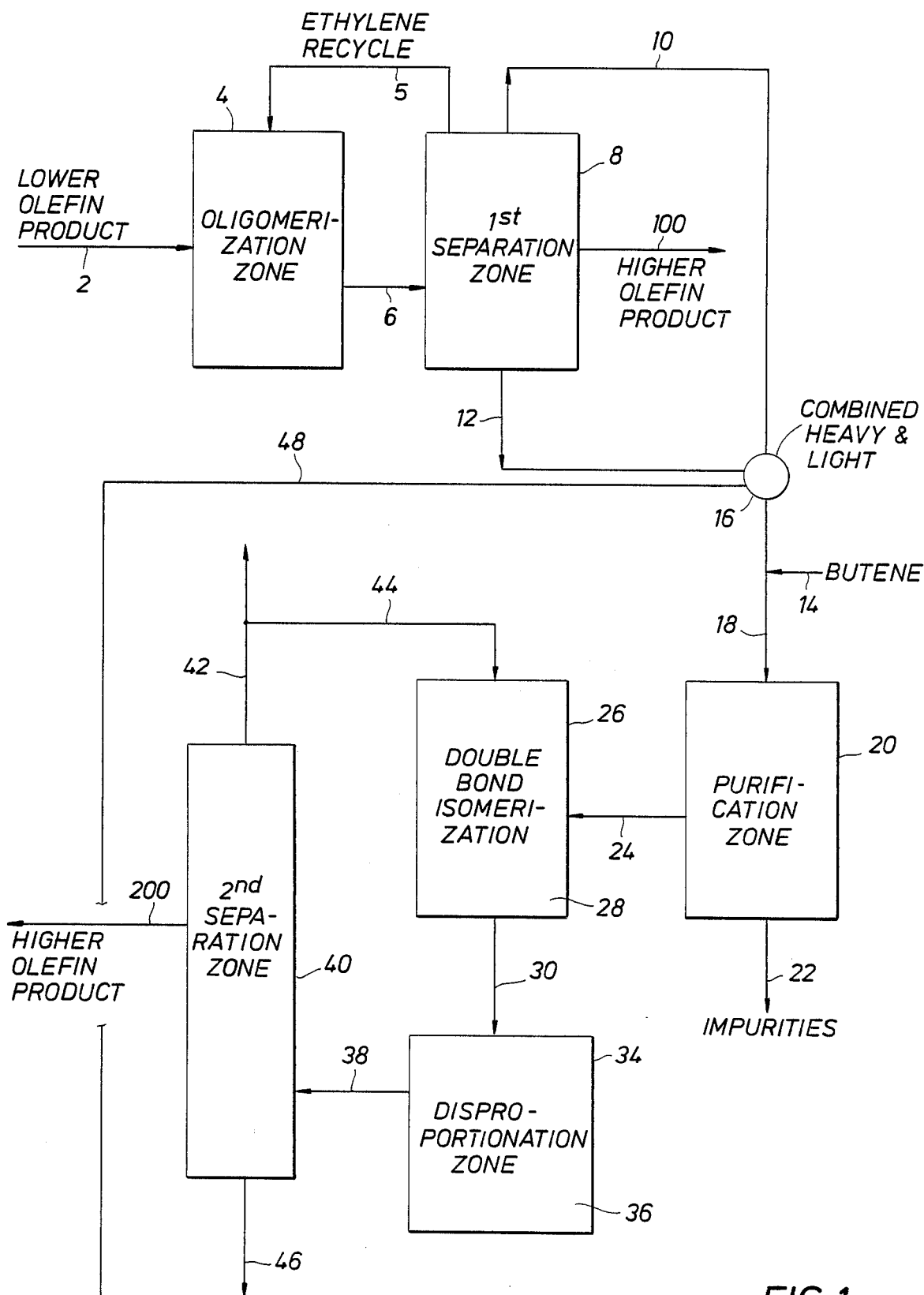
FIG. 1 is a schematic flow scheme of one embodiment of the process of this invention.

The instant flow scheme derives two higher olefin product streams from respective separation zones 8 and 40, i.e. high olefin product stream 100 and high olefin product stream 200. These streams are derived by first charge to oligomerization zone 4 of a lower olefin, preferably ethylene, via conduit 2. The oligomerization zone is maintained in the presence of an oligomerization catalyst to maximize where possible the quantity of $C_{12}$ to $C_{18}$ olefins. The effluent from the oligomerization zone is passed through conduit 6 containing olefins from $C_2$ to $C_{100}$ which necessitate separation. This is accomplished in first separation zone 8 maintained under conditions sufficient to maximize separation of a $C_{12}$ to $C_{18}$ first olefin product stream in conduit 100. This product may be either further processed to alcohols or aldehydes, or if desired, sold as is. A light olefin top stream is derived from the first separation zone and comprises an ethylene recycle stream removed through conduit 5, light alpha olefins having from $C_4$ up to $C_{10}$ removed through conduit 10, while a bottoms stream is removed via conduit 12 containing olefins having from $C_{20}$ to $C_{100}$ If desired, all or a portion of the light olefin stream may be sold for its indigenous hydrocarbon qualities. The continued processing of at least one and preferably both of these two flotsam streams, 10 and 12, is the linchpin to the economic prowess of the overall select olefin production of this process. These streams are combined with the addition of butene added by conduit 14 after their admixture in a zone or area generally nomenclated as 16 in the instant drawing. It is conceivable that a recycle stream may be provided from the second separation zone via 48 and thereafter butene is added to equate the average molecular weight of the olefin materials to approximately $C_{12}$. These olefins are passed in accompaniment with certain undesirable impurities to a purification zone wherein an absorbent bed selective for absorption of the impurities is provided. This absorption bed can be an inorganic refractory oxide, such as alumina or another type of molecular sieve whereby oxygenates, metal ions, water, inorganics and other unwanted impurities are absorbed to provide a cleansing of the overall olefin feed charged to purification zone 20 in conduit 18. Intermittenly, impurities may be removed from the absorbent zone via removal conduit 22 and the absorption zone either be replaced or the absorbent bed regenerated by means not shown in the instant drawing. The effluent from purification zone 24, is charged to double bond isomerization zone 26 containing the select aluminosilicate channel size sieve generally shown as 28 with a silylated surface. These sieves are carefully selected for permitting and encouraging the isomerization of the alpha olefins to an internal position commensurate with prohibiting alkylation and/or aromatization of the olefins in the sieve. The sieve is preferrably an 8 and 10 member ring aluminosilicate. After silylation, the amount of dimerization which occurs during isomerization is reduced. The effluent from double bond isomerization zone 26 is withdrawn through conduit 30 and passed to disproportionation zone 34. In the disproportionation zone two molecules of internal olefins disproportionate to produce higher and lower internal olefinic products. The olefins, which are not considered alpha olefins, will be isomerized to the alpha position either during disproportionation or will be so isomerized during subsequent hydroformylation in the presence of a hydroformylation catalyst. The disproportionation zone will also contain a disproportionation catalyst 36. The effluent from the disproportionation zone contains olefins having a carbon number of from 4 to 100. The disproportionation zone is maintained at conditions to maximize the quantity of $C_{12}$ to $C_{18}$ olefins. The disproportionation zone effluent 38 is passed to a second separation zone 40 maintained at conditions effective to separate a $C_{12}$ to $C_{18}$ higher olefin product in conduct 200. A light olefin material having a carbon number from $C_2$ to $C_{10}$ is withdrawn from the second separation zone 40 in conduit 42 and a portion of the same may be recycled to the double bond isomerization zone 26 by means of conduit 44. A heavy olefin material is withdrawn from the second separation zone 40 through conduit 46 and a portion of the same may be admixed with the combined light and heavy olefins separated from the first separation zone 8 in mixing area 16 by means of conduit 48.

The instant drawings have been provided as a schematic scheme to exemplify the process of this invention and should not be construed as a limitation thereupon.

Illustrative Embodiments

EXAMPLE 1

This example is offered to show the viability of an 8 and 10 member ring aluminosilicate catalyst for isomerization of terminal to internal olefins. This example is used as a comparison with examples which follow to appreciate the reduction in dimerization during isomerization derivative of silylation of the surface of the catalyst.

The catalyst utilized in this example is a piperdine derived ferrierite catalyst as disclosed in U.S. Pat. No. 4,343,692 and prepared by the technique of U.S. Pat. No. 4,251,499. The ammonium ferrierite was converted to an acidic hydrogen form by calcination in air at 550° C. for two hours. Thereafter, 20 cc of undiluted hydrogen ferrierite was loaded into a reactor and pretreated at 975° F. for 10 hours under flowing nitrogen. The catalyst was cooled under nitrogen to 150° F. and 1-decene was introduced as exemplary of an alpha olefin reactant. Data collected at 150° F., 200° F. and 250° F. are exemplified in Tables 1 and 2.

TABLE 1

| ISOMERIZATION ACTIVITY WITH DIMERIZATION | | | | |
|---|---|---|---|---|
| Catalyst | Reactor Temp. F. | WHSV | Percent Isomerization | Percent Dimerization |
| Ferrierite (1) | 150 | 1.63 | 93.2 | 4.70 |
| Ferrierite (2) | 200 | 1.94 | 100.6 | 5.72 |
| Ferrierite (3) | 250 | 1.67 | 102.3 | 10.26 |
| Ferrierite (4) | 250 | 11.40 | 102.4 | 4.81 |

TABLE 2

| NORMALIZED MOLE PERCENT $C_{10}$ OLEFIN ISOMERS | | | | |
|---|---|---|---|---|
| Double Bond Position | Ferrierite/ (1) | Ferrierite/ (2) | Ferrierite/ (3) | Ferrierite/ (4) |
| 5 | 10.7 | 13.9 | 14.8 | 14.9 |
| 4 | 26.5 | 31.3 | 32.4 | 32.7 |

TABLE 2-continued

| NORMALIZED MOLE PERCENT $C_{10}$ OLEFIN ISOMERS | | | | |
|---|---|---|---|---|
| Double Bond Position | Ferrierite/ (1) | Ferrierite/ (2) | Ferrierite/ (3) | Ferrierite/ (4) |
| 3 | 26.7 | 24.6 | 24.3 | 23.8 |
| 2 | 35.2 | 28.9 | 26.4 | 26.5 |
| 1 | 0.8 | 1.3 | 2.1 | 2.1 |
| Beta/Alpha | 44.0 | 22.2 | 12.6 | 12.6 |

EXAMPLE 2

The catalyst used in this example is commensurate with the ferrierite catalyst of Example 1 with the exception that the ferrierite catalyst is doped with palladium as shown in U.S. Pat. No. 4,343,692. In this instance the ammonium form of the ferrierite was exchanged with a 2M soln. of $Pd(NH_3)_4(NO_3)_2$ prior to pretreatment. The material was then pretreated, as in Example 1, with the exception that a reduction of the $Pd(2+)$ ion was effected by passage of hydrogen over the catalyst at atmospheric pressure for 2 hrs. at 650° F. prior to introduction of the 1-decene feed. Data collected at 205° F. are exemplified in Tables 3 and 4.

TABLE 3

| ISOMERIZATION ACTIVITY | | | | |
|---|---|---|---|---|
| Catalyst | Temp °F. | WHSV | Percent Isomerization | Percent Dimerization |
| Ferrierite/Pd(1) | 205 | 2.3 | 101.7 | 2.49 |
| Ferrierite/Pd(2) | 205 | 4.7 | 92.2 | 1.23 |

TABLE 4

| NORMALIZED MOLE PERCENT $C_{10}$ ISOMERS | | |
|---|---|---|
| Double Bond Position | Ferrierite/Pd (1) | Ferrierite/Pd (2) |
| 5 | 14.7 | 10.9 |
| 4 | 31.9 | 26.3 |
| 3 | 24.1 | 25.7 |
| 2 | 27.5 | 34.1 |
| 1 | 1.8 | 2.3 |
| Beta/Alpha | 15.3 | 14.5 |

The data presented in Table 5 below illustrate that the dimerization of olefins on ferrierite is catalyzed by Bronsted acid sites located on the surface of the zeolite rather than in the zeolite channels. The small size of the ferrierite channel restricts the formation of any dimers which might otherwise form via an acid catalyzed alkylation reaction pathway. It is known that pyridine is a Bronsted acid poison. Furthermore, the pyridine molecule is too large to enter into the pores of the ferrierite. Therefore, by spiking the olefin feed stream with pyridine, the acid sites located on the surface of ferrierite can be selectively poisoned. This selective poisoning allows those reactions which occur both on the surface and in the channels of the ferrierite to be differentiated from those which occur only on the zeolite surface. The data shown were collected at 350° F.

TABLE 5

| ACID SITE POISONING WITH PYRIDINE | | |
|---|---|---|
| Feed | % Double Bond Isomerization | % Dimer Formation |
| 1-Decene | 100.3 | 1.41 |
| 1-Decene with 100 ppm Pyridine | 28.3 | 0.00 |

EXAMPLE 4

Example 3 above demonstrates that the dimerization reaction which occurs during isomerization can be controlled by in situ poisoning of the acid sites located on the external surfaces of the ferrierite catalyst. This example demonstrates that when these external acid sites are poisoned selectively via silylation then the dimerization reaction can be mitigated while isomerization takes place.

A 12.1 gram sample of 16-45 mesh ammonium ferrierite as used in Example 1 is converted to its hydrogen form by calcination in air at 550° C. for two hours. The ferrierite was suspended in 100 ml of hexene to which 8 grams of 1,1,1,3,3,3-hexamethyldisilazane (HMDS) was added. The reactants were refluxed for one hour followed by filtering and washing four times with 75 mls. of hexane. This produced a silylated ferrierite having a surface acid sites poisoned by reaction with the HMDS molecule. The silylated ferrierite was then dried at 120° C. under flowing nitrogen. Approximately 20 cc of the finished silylated catalyst was loaded into a reactor to determine isomerization activity. The catalyst was maintained at 200° F. under nitrogen pressure while an olefin, 1-decene, was introduced to the catalyst. Table 6 set forth below demonstrates the isomerization and dimerization which occurred in the presence of the silylated hydrogen ferrierite.

TABLE 6

| | | | | Silylated H+ Ferrierite | | | | |
|---|---|---|---|---|---|---|---|---|
| Exp. No. | Tem. F. | Cat. Hrs. | WHSV | % C10 DB Iso. | % Dimer | % C10 Branch | Net C10 Branch | NetBrch/ Dimer |
| 1 | 75 | 0 | 0.0 | 2.5 | 0.00 | 1.57 | 0.00 | NA |
| 2 | 201 | 42 | 1.4 | 32.7 | 0.26 | 1.64 | 0.07 | 0.27 |
| 3 | 200 | 66 | 2.3 | 14.9 | 0.12 | 1.58 | 0.01 | 0.08 |
| 4 | 252 | 90 | 2.7 | 39.5 | 0.15 | 1.67 | 0.10 | 0.66 |
| 5 | 303 | 162 | 2.5 | 61.1 | 0.17 | 1.86 | 0.29 | 1.72 |
| 6 | 354 | 186 | 2.5 | 91.0 | 0.23 | 3.52 | 1.95 | 8.48 |
| 7 | 354 | 210 | 2.6 | 99.8 | 0.14 | 3.73 | 2.16 | 15.43 |
| 8 | 370 | 234 | 2.6 | 100.2 | 0.09 | 3.67 | 2.10 | 23.33 |
| 9 | 369 | 258 | 2.6 | 99.0 | 0.04 | 2.90 | 1.33 | 33.25 |
| 10 | 368 | 330 | 2.8 | 87.3 | 0.00 | 2.21 | 0.64 | NA |
| 11 | 368 | 354 | 1.7 | 88.3 | 0.00 | 2.11 | 0.54 | NA |
| 12 | 368 | 378 | 3.0 | 66.7 | 0.02 | 1.75 | 0.18 | 9.00 |
| 13 | 368 | 404 | 2.5 | 73.0 | 0.00 | 1.94 | 0.37 | NA |
| 14 | 384 | 426 | 2.5 | 87.9 | 0.33 | 2.19 | 0.62 | 1.88 |
| 15 | 385 | 498 | 2.5 | 89.7 | 0.00 | 2.15 | 0.58 | NA |
| 16 | 384 | 522 | 2.5 | 91.3 | 0.01 | 2.21 | 0.64 | 64.00 |
| 17 | 403 | 546 | 2.5 | 98.8 | 0.00 | 3.66 | 2.09 | NA |
| 18 | 404 | 571 | 2.5 | 99.9 | 0.05 | 3.20 | 1.63 | 30.75 |
| 19 | 404 | 597 | 2.5 | 99.7 | 0.05 | 3.43 | 1.86 | 35.77 |

TABLE 6-continued

| | | | Silylated H+ Ferrierite | | | | |
|---|---|---|---|---|---|---|---|
| Exp. No. | Tem. F. | Cat. Hrs. | WHSV | % C10 DB Iso. | % Dimer | % C10 Branch | Net C10 Branch | NetBrch/ Dimer |
| 20 | 404 | 667 | 2.6 | 99.6 | 0.01 | 3.29 | 1.72 | 172.00 |
| 21 | 404 | 690 | 2.7 | 99.5 | 0.02 | 3.31 | 1.74 | 108.75 |
| 22 | 403 | 714 | 2.7 | 99.6 | 0.01 | 3.33 | 1.76 | 176.00 |
| 23 | 403 | 738 | 2.5 | 99.5 | 0.02 | 3.39 | 1.82 | 113.75 |
| 24 | 404 | 762 | 2.4 | 99.9 | 0.01 | 3.49 | 1.92 | 192.00 |
| 25 | 404 | 834 | 2.3 | 99.1 | 0.01 | 3.24 | 1.67 | 151.82 |
| 26 | 404 | 858 | 2.4 | 98.8 | 0.02 | 3.02 | 1.45 | 96.67 |
| 27 | 403 | 882 | 2.4 | 98.5 | 0.01 | 2.98 | 1.41 | 141.00 |
| 28 | 403 | 906 | 2.5 | 98.5 | 0.02 | 2.95 | 1.38 | 86.25 |
| 29 | 404 | 930 | 2.5 | 98.2 | 0.01 | 2.89 | 1.32 | 94.29 |

NA = Not available.

Table 7 shows the olefin double bond distribution of the isomerized $C_{10}$ product over a silylated hydrogen ferrierite.

TABLE 7

Olefin Double Bond Distribution of Isomerized C10 over Silylated H+ Ferrierite using 1-Decene Feed.

| Test No. | % C10 DB Iso. | 1-C10 | 2-C10 | 3-C10 | 4-C10 | 5-C10 | Beta/ Alpha |
|---|---|---|---|---|---|---|---|
| 1 | 2.5 | 97.1 | 1.4 | 0.0 | 1.3 | 0.1 | .0 |
| 2 | 32.7 | 50.4 | 33.5 | 9.7 | 5.0 | 1.5 | 0.7 |
| 3 | 14.9 | 74.7 | 19.5 | 3.6 | 1.7 | 0.5 | 0.3 |
| 4 | 39.5 | 42.5 | 36.2 | 12.7 | 6.6 | 2.0 | 0.9 |
| 5 | 61.1 | 26.1 | 35.2 | 18.4 | 14.5 | 5.7 | 1.3 |
| 6 | 91.0 | 7.1 | 31.0 | 23.1 | 26.9 | 12.0 | 4.4 |
| 7 | 99.8 | 3.9 | 26.8 | 23.3 | 31.5 | 14.5 | 6.9 |
| 8 | 100.2 | 4.0 | 26.4 | 23.2 | 31.6 | 14.8 | 6.6 |
| 9 | 99.0 | 4.1 | 27.4 | 23.5 | 30.8 | 14.3 | 6.7 |
| 10 | 87.3 | 7.5 | 32.9 | 24.5 | 24.8 | 10.3 | 4.4 |
| 11 | 88.3 | 6.2 | 33.2 | 25.0 | 25.4 | 10.1 | 5.4 |
| 12 | 66.7 | 24.2 | 31.4 | 20.3 | 17.4 | 6.7 | 1.3 |
| 13 | 73.0 | 13.7 | 38.7 | 23.0 | 17.9 | 6.7 | 2.8 |
| 14 | 87.9 | 7.2 | 33.0 | 24.1 | 25.0 | 10.7 | 4.6 |
| 15 | 89.7 | 6.3 | 32.4 | 24.3 | 25.6 | 11.3 | 5.1 |
| 16 | 91.3 | 5.8 | 31.9 | 24.3 | 26.3 | 11.8 | 5.5 |
| 17 | 98.8 | 4.0 | 27.5 | 23.5 | 30.5 | 14.4 | 6.9 |
| 18 | 99.9 | 4.4 | 26.3 | 23.1 | 31.3 | 14.9 | 6.0 |
| 19 | 99.7 | 4.3 | 26.5 | 23.2 | 31.2 | 14.8 | 6.2 |
| 20 | 99.6 | 4.3 | 26.6 | 23.2 | 31.1 | 14.8 | 6.2 |
| 21 | 99.5 | 4.4 | 26.6 | 23.2 | 31.1 | 14.7 | 6.0 |
| 22 | 99.6 | 4.3 | 26.4 | 23.2 | 31.3 | 14.7 | 6.1 |
| 23 | 99.5 | 4.4 | 26.4 | 23.2 | 31.2 | 14.7 | 6.0 |
| 24 | 99.9 | 4.3 | 26.3 | 23.3 | 31.4 | 14.8 | 6.1 |
| 25 | 99.1 | 4.7 | 26.6 | 23.1 | 31.0 | 14.6 | 5.7 |
| 26 | 98.8 | 4.5 | 27.1 | 23.3 | 30.6 | 14.5 | 6.0 |
| 27 | 98.5 | 4.5 | 27.1 | 23.4 | 30.5 | 14.4 | 6.0 |
| 28 | 98.5 | 4.6 | 27.3 | 23.4 | 30.4 | 14.4 | 5.9 |
| 29 | 98.2 | 4.7 | 27.3 | 23.4 | 30.3 | 14.3 | 5.8 |

These tables, when compared with those of Example 1, i.e., Tables 1 and 2, show that silylating the acidic hydrogen ferrierite reduces greatly the dimerization reaction which occurs during isomerization absent silylation. For example, a dimer concentration of only 0.26% is determined in Test No. 2 in comparison with the 4 to 10% dimerization activity found using the unsilylated hydrogen ferrierite isomerization catalyst.

EXAMPLE 5

In this example, 50 grams of the ammonium form of ferrierite was ion exchanged with tetraamine palladium (II) nitrate at room temperature for two hours. The catalyst was then dried under reduced nitrogen pressure at 120° C. The palladium exchanged ferrierite was then pressed, sized to 16 to 45 mesh and silylated by refluxing with HMDS in hexane for 30 minutes. The silylated catalyst was washed with hexane and dried overnight at 120° C. under nitrogen pressure.

Twenty cc of the silylated palladium hydrogen ferrierite was loaded in a reactor and reduced under the flow of hydrogen at 650° F. for one hour. The catalyst was cooled to 200° F. before purified 1-decene feed was introduced. The isomerization and dimerization activities of this catalyst are set forth in Table 8 with the olefin bond distribution set forth in Table 9.

TABLE 8

| | | | Silylated Pd/Ferrierite | | | | | | |
|---|---|---|---|---|---|---|---|---|---|
| Test No. | Temp. °F. | Cat. Hrs. | WHSV | % C10 TLP | % C10 DB Iso. | % Dimer | % C10 Branch | Net C10 Branch | % Dimer/ % Branch. |
| 1 | NA | 0 | NA | 99.55 | 2.50 | 0.00 | 1.57 | 0.00 | 0.00 |
| 2 | 201 | 19 | 2.1 | 98.67 | 95.40 | 1.07 | 2.36 | 0.79 | 0.45 |
| 3 | 202 | 43 | 2.4 | 98.83 | 93.70 | 0.91 | 2.17 | 0.60 | 0.42 |
| 4 | 212 | 67 | 2.6 | 98.93 | 93.70 | 0.80 | 2.18 | 0.61 | 0.37 |
| 5 | 212 | 91 | 2.7 | 99.02 | 92.40 | 0.72 | 2.18 | 0.61 | 0.33 |
| 6 | 231 | 168 | 2.6 | 98.68 | 96.40 | 0.60 | 2.20 | 0.63 | 0.27 |
| 7 | 231 | 188 | 2.7 | 99.13 | 95.10 | 0.61 | 2.19 | 0.62 | 0.28 |
| 8 | 253 | 211 | 2.7 | 99.03 | 99.20 | 0.67 | 2.52 | 0.95 | 0.26 |
| 9 | 253 | 275 | 2.7 | 99.07 | 97.30 | 0.62 | 2.35 | 0.78 | 0.26 |
| 10 | 253 | 299 | 2.7 | 99.15 | 95.90 | 0.60 | 2.25 | 0.68 | 0.27 |
| 11 | 254 | 323 | 2.7 | 99.17 | 93.90 | 0.57 | 2.20 | 0.63 | 0.26 |
| 12 | 277 | 347 | 2.7 | 99.11 | 95.70 | 0.61 | 2.31 | 0.74 | 0.27 |
| 13 | 278 | 371 | 2.7 | 99.09 | 97.30 | 0.65 | 2.34 | 0.77 | 0.28 |
| 14 | 302 | 446 | 2.7 | 99.02 | 98.60 | 0.67 | 2.36 | 0.79 | 0.28 |
| 15 | 302 | 467 | 2.6 | 99.02 | 97.10 | 0.67 | 2.31 | 0.74 | 0.29 |
| 16 | 302 | 491 | 2.6 | 99.04 | 96.30 | 0.65 | 2.24 | 0.67 | 0.29 |
| 17 | 302 | 515 | 2.4 | 99.08 | 95.00 | 0.65 | 2.19 | 0.62 | 0.29 |

TABLE 8-continued

Silylated Pd/Ferrierite

| Test No. | Temp. °F. | Cat. Hrs. | WHSV | % C10 TLP | % C10 DB Iso. | % Dimer | % C10 Branch | Net C10 Branch | % Dimer/ % Branch. |
|---|---|---|---|---|---|---|---|---|---|
| 18 | 302 | 539 | 2.4 | 99.06 | 93.20 | 0.61 | 2.14 | 0.57 | 0.29 |
| 19 | 304 | 611 | 2.5 | 99.17 | 90.30 | 0.53 | 2.13 | 0.56 | 0.25 |
| 20[1] | 304 | 619 | 2.5 | 99.03 | 86.90 | 0.52 | 2.05 | 0.48 | 0.25 |
| 21 | 206 | 640 | 2.5 | 97.11 | 100.40 | 2.59 | 2.45 | 0.88 | 1.06 |
| 22 | 205 | 664 | 2.5 | 97.63 | 100.50 | 2.08 | 2.30 | 0.73 | 0.90 |
| 23[2] | 205 | 688 | 2.5 | 97.82 | 100.30 | 1.82 | 2.30 | 0.73 | 0.79 |
| 24 | 205 | 708 | 2.5 | 98.73 | 101.00 | 0.89 | 2.65 | 1.08 | 0.34 |
| 25 | 205 | 732 | 2.5 | 98.96 | 100.00 | 0.65 | 2.44 | 0.87 | 0.27 |
| 26 | 205 | 756 | 2.4 | 99.05 | 97.10 | 0.55 | 2.39 | 0.82 | 0.23 |
| 27 | 205 | 780 | 2.4 | 98.93 | 98.20 | 0.69 | 2.45 | 0.88 | 0.28 |
| 28 | 204 | 853 | 2.4 | 99.08 | 97.10 | 0.56 | 2.40 | 0.83 | 0.23 |
| 29 | 205 | 876 | 2.4 | 98.99 | 96.50 | 0.63 | 2.45 | 0.88 | 0.26 |
| 30 | 204 | 900 | 2.2 | 99.05 | 96.60 | 0.54 | 2.31 | 0.74 | 0.23 |

[1] Test 20 = catalyst regeneration with nitrogen stripping at 975° F. for 10 hours.
[2] Test 23 = catalyst nitrogen stripped at 400° F. for 3 hours prior to reactor shutdown.

TABLE 9

Olefin Double Bond Distribution of Isomerized C10 Product Obtained over Silylated Pd/Ferrierite using 1-Decene Feed.

| Test No. | Reax. Temp. F. | % C10 DB Iso. | 1-C10 | 2-C10 | 3-C10 | 4-C10 | 5-C10 | Beta/ Alpha |
|---|---|---|---|---|---|---|---|---|
| 1 | NA | 2.50 | 97.10 | 1.40 | 0.00 | 1.30 | 0.10 | 0.01 |
| 2 | 201 | 95.40 | 5.10 | 29.40 | 23.80 | 28.40 | 13.40 | 5.76 |
| 3 | 202 | 93.70 | 3.20 | 32.90 | 24.80 | 27.20 | 12.00 | 10.28 |
| 4 | 212 | 93.70 | 3.20 | 32.90 | 24.90 | 26.90 | 12.10 | 10.28 |
| 5 | 212 | 92.40 | 3.50 | 33.70 | 24.90 | 26.30 | 11.60 | 9.63 |
| 6 | 231 | 96.40 | 2.90 | 30.80 | 24.60 | 28.80 | 12.90 | 10.62 |
| 7 | 231 | 95.10 | 3.10 | 31.80 | 24.80 | 27.90 | 12.50 | 10.26 |
| 8 | 253 | 99.20 | 2.80 | 28.50 | 24.10 | 30.50 | 14.10 | 10.18 |
| 9 | 253 | 97.30 | 3.10 | 29.80 | 24.40 | 29.30 | 13.40 | 9.61 |
| 10 | 253 | 95.90 | 3.10 | 31.00 | 24.60 | 28.40 | 12.90 | 10.00 |
| 11 | 254 | 93.90 | 3.20 | 32.40 | 24.80 | 27.50 | 12.00 | 10.12 |
| 12 | 277 | 95.70 | 3.20 | 31.00 | 24.50 | 28.60 | 12.70 | 9.69 |
| 13 | 278 | 97.30 | 3.00 | 29.90 | 24.40 | 29.40 | 13.30 | 9.97 |
| 14 | 302 | 98.60 | 3.20 | 28.60 | 24.00 | 30.30 | 13.90 | 8.94 |
| 15 | 302 | 97.10 | 3.30 | 29.60 | 24.20 | 29.50 | 13.30 | 8.97 |
| 16 | 302 | 96.30 | 3.40 | 30.20 | 24.40 | 29.00 | 13.00 | 8.88 |
| 17 | 302 | 95.00 | 3.50 | 31.20 | 24.60 | 28.20 | 12.50 | 8.91 |
| 18 | 302 | 93.20 | 3.70 | 32.40 | 24.80 | 27.20 | 11.80 | 8.76 |
| 19 | 304 | 90.30 | 4.10 | 34.70 | 24.90 | 25.40 | 10.90 | 8.46 |
| 20 | 304 | 86.90 | 4.50 | 37.10 | 25.10 | 23.50 | 9.70 | 8.24 |
| 21 | 206 | 100.40 | 3.40 | 27.10 | 23.50 | 31.30 | 14.80 | 7.97 |
| 22 | 205 | 100.50 | 2.60 | 27.70 | 23.90 | 31.20 | 14.60 | 10.65 |
| 23 | 205 | 100.30 | 2.40 | 28.10 | 24.20 | 31.00 | 14.40 | 11.71 |
| 24 | 205 | 101.00 | 2.20 | 27.80 | 24.00 | 31.40 | 14.70 | 12.64 |
| 25 | 205 | 100.00 | 2.10 | 28.70 | 24.40 | 30.60 | 14.20 | 13.67 |
| 26 | 205 | 97.10 | 3.50 | 28.90 | 24.90 | 29.90 | 12.80 | 8.26 |
| 27 | 205 | 98.20 | 2.10 | 30.00 | 24.80 | 29.60 | 13.50 | 14.29 |
| 28 | 204 | 97.10 | 2.20 | 30.80 | 25.00 | 28.90 | 13.00 | 14.00 |
| 29 | 205 | 96.50 | 2.20 | 31.30 | 25.10 | 28.70 | 12.70 | 14.23 |
| 30 | 204 | 96.60 | 2.20 | 31.20 | 25.10 | 28.70 | 12.80 | 14.18 |

(1) Catalyst regeneration initiated, nitrogen strip at 975° F. for 10 hrs.
(2) Catalyst nitrogen stripped at 400° F. for 3 hrs. prior to shutdown.

A comparison of the results of Tables 8 and 9 versus Tables 3 and 4 show a drastic reduction in dimerization activity. Silylation dramatically reduces the production of undesirable products via dimerization by selectively deactivating surface active sites.

I claim as my invention:

1. A double bond isomerization process for the movement of a double bond possessed by an alpha olefinic molecule from the alpha position to an interior position in said molecule, which process comprises contacting at least one of said olefin having an alpha double bond therein with a select aluminosilicate having 8 and 10 member ring channels of a size sufficient to permit said double bond isomerization and a size restrictive to prohibit aromatization or alkylation of said olefin molecule within said channels of said aluminosilicate, wherein said aluminosilicate is treated with a silylation agent prior to contact with said alpha olefin, at isomerization conditions, to thereby move said double bond from said alpha position to an interior position.

2. The process of claim 1 wherein said isomerization conditions include a temperature of from 0° C. to about 500° C., a pressure of from about 1.0 psia to about 2000 psia and a weight hourly space velocity of from 0.1 to about 20.

3. The process of claim 1 wherein said select sufficient 8 and 10 member ring channel size aluminosilicate is selected from the group consisting of ferrierite, ZSM-35, and mixtures thereof.

4. The process of claim 1 wherein said silylation agent comprises organofunctional silylation agents.

5. The process of claim 4 wherein said organofunctional silylation agent is 1,1,1,3,3,3,-hexamethyldisilazane.

6. The process of claim 4 wherein said organofunctional silylation agent comprises:

$$SiR_yX_{4-y} \text{ or } (RwX_{3-w}Si)_2\text{-}Z;$$

wherein
y=1 to 4
w=1 to 3
R=alkyl, aryl, alkoxy, arylalkyl moieties having from 1 to 10 carbon atoms
x=halide and
Z=oxygen, NH— or substituted amines and amides.

7. The process of claim 1 wherein said olefinic molecule has from $C_4$ and $C_{100}$ carbon atoms.

8. The process of claim 5 wherein said olefinic molecules comprise a blend of olefins having $C_4$, $C_6$ to $C_{10}$ and $C_{15}$ to $C_{60}$ carbon atoms with the addition of $C_4$ olefins to balance the average carbon number distribution to about $C_{12}$.

9. The process of claim 1 wherein the distribution of internal olefins prepared from $C_{10}$ alpha olefin isomerization is, at equilibrium, equal to about 20% to 30% at the 8 and 2 position, about 20% to 25% at the 7 and 3 position, about 25% to 35% at the 6 and 4 position and about 10% to 15% at the 5 position, wherein said isomer distribution is attained at 25 to 100% of a calculated isomer distribution.

10. The process of claim 3 wherein said select aluminosilicate catalyst has associated therewith a metal selected from Group VIII of the Periodic Table.

11. The process of claim 8 wherein said metal selected from Group VIII of the Periodic Table is palladium.

12. The process of claim 9 wherein said palladium is present in an amount of from 0.01% to about 10% on the basis of the total weight of the catalyst.

13. The process of claim 1 wherein said treatment of said aluminosilicate with said silylation agents is sufficient to modify the surface of said aluminosilicate and to thereby reduce dimerization reactions during said isomerization of said alpha olefins.

14. A process for the increased production of higher olefins having alpha double bonds from ethylene which comprises:
(a) oligomerization of a feed material predominately comprising ethylene in an ethylene oligomerization zone, at oligomerization conditions, in the presence of an oligomerization catalyst, to form higher olefinic molecules having even carbon numbers of from $C_4$ to $C_{100}$;
(b) separating said produced even numbered olefins in a first separation zone, at first separation zone conditions, to form a first olefin product stream having alpha double bonds and having from $C_{12}$ to $C_{18}$ and first separation zone effluent stream having: (1) unreacted ethylene, (2) light alpha olefins of from $C_4$ to $C_{10}$ and (3) heavy alpha olefins having from $C_{20}$ to $C_{100}$;
(c) combining said light and said heavy alpha olefins and passing said combined stream to purification-isomerization-disproportionation steps and balancing therewith a quantity of $C_4$ olefins to average the carbon number in said combined stream to approximately $C_{12}$;
(d) purifying said combined alpha olefin stream in the presence of a purification absorbent bed, at purification conditions, to remove from said combined stream impurities comprising oxygenates, metals, water and inorganics;
(e) double bond isomerizing, in an isomerization step, said purified alpha olefins of step (d), at isomerization conditions, in the presence of a select aluminosilicate catalyst having 8 and 10 member ring channels of a size sufficient to permit said isomerization and a size restrictive to prohibit aromatization or alkylation of said olefin molecule within said channels of said aluminosilicate wherein said aluminosilicate is treated prior to isomerization of said alpha olefins with a silylation agent to modify the surface of the aluminosilicate and to thereby diminish the amount of dimerization during isomerization, wherein said isomerization produces isomerization effluent stream having internal double bonds and being substantially free of alpha-situated double bonds;
(f) disproportionating said isomerization olefin stream produced in step (e) in a disproportionation step in the presence of a disproportionation catalyst maintained at disproportionation conditions, to form an effluent stream containing $C_{12}$–$C_{18}$ olefins and olefins lighter and heavier than $C_{12}$ and $C_{18}$; and
(g) separating said disproportionation effluent stream of step (f) in a second separation zone maintained at second separation conditions to form a second olefin product stream having from $C_{10}$–$C_{18}$ carbon atoms and to a light and heavy olefin fraction.

15. The process of claim 14 wherein said oligomerization catalyst comprises an organometallic compound and wherein said oligomerization conditions comprise a temperature of 0° C. to about 250° C. and a pressure of from about 14 psig to about 3000 psig.

16. The process of claim 15 further characterized in that said oligomerization catalyst comprises an aluminum trialkyl wherein ethylene is oligomerized in the presence of said catalyst at a temperature of about 25° C. and a pressure of about 550 psig.

17. The process of claim 15 wherein said oligomerization catalyst is prepared by contacting bis-1,5-cyclooctadiene nickel and diphenylcarboxymethylphosphine.

18. The process of claim 14 wherein said first separation zone is maintained at a temperature of about −10° C. to about 300° C. and a pressure of from about 0.4 psia to about 650 psig to form said first olefin product stream having alpha double bonds and said first separation zone effluent streams having light alpha olefins of from $C_4$ to $C_{10}$ and heavy alpha olefins having from $C_{20}$ to $C_{100}$ carbon atoms.

19. The process of claim 14 wherein said purification absorbent bed comprises a refractory inorganic oxide.

20. The process of claim 19 wherein said refractory inorganic oxide comprises alumina, silica, zirconia, magnesia, silica-alumina and silica-alumina-chromia.

21. The process of claim 14 wherein said purification conditions include a temperature of about 100° C. to about 200° C. and a pressure of from about 1 psig to about 200 psig.

22. The process of claim 19 wherein said refractory inorganic oxide is selected for absorption of impurities comprising oxygenates, metallic ions, water and inorganics.

23. The process of claim 14 wherein said select aluminosilicate catalyst is selected from the group consisting of ferrierite, ZSM-35 and mixtures thereof.

24. The process of claim 14 wherein said distribution of internal olefins prepared from the isomerization of a $C_{10}$ alpha olefin is, at equilibrium, equal to about 20% to about 30% at the 8 and 2 position, about 20% to 25% at the 7 and 3 position, about 25% to 35% at the 6 and 4 position and about 10% to about 15% at the 5 position, wherein said isomerization distribution is attained at 80 to 100% of the calculated isomer distribution.

25. The process of claim 14 wherein said disproportionation catalyst comprises a Group VIB or a combination of Group VIB metals supported on an inorganic oxide support.

26. The process of claim 25 wherein said inorganic oxide support has been treated with alkali or alkaline earth metal compounds.

27. The process of claim 14 wherein said disproportionation conditions include a temperature of from about 100° C. to about 150° C. and a pressure of from about 10 psig to about 250 psig.

28. The process of claim 14 wherein said separation in said second separation zone is performed under second separation conditions including a temperature of 30° C. to about 350° C. and a pressure of from about 1 psia to about 200 psig.

29. The process of claim 14 wherein said light olefin fraction produced in step (g) is recycled to said disproportionation of step (f) or said isomerization of step (e).

30. The process of claim 14 wherein said heavy olefin fraction separated in step (g) is recycled to said combined light and heavy alpha olefin in step (c) and passed to said purification-isomerization-disproportionation steps.

31. The process of claim 14 wherein said isomerization conditions include a temperature of from about 100° C. to about 150° C. and a pressure of from about 10 psig to about 250 psig.

32. The process of claim 14 wherein said unreacted ethylene acquired in said first separation zone is recycled to said oligomerization of step (a).

33. The process of claim 14 wherein said silylation is performed by contacting said select aluminosilicate with a silylation agent comprising an organofunctional silylation agent.

34. The process of claim 33 wherein said organofunctional silylation agent is selected from the group consisting of 1,1,1,3,3,3,-hexamethyldisilazane, trimethylchlorosilane, dimethylchlorosilane, and bis(trimethylsilyl)acteamide.

* * * * *